US012580064B2

(12) United States Patent
Donzelli et al.

(10) Patent No.: US 12,580,064 B2
(45) Date of Patent: Mar. 17, 2026

(54) METHOD FOR DETERMINING A TREATMENT PLAN INCLUDING A DOSE DISTRIBUTION

(71) Applicant: Brainlab SE, Munich (DE)

(72) Inventors: Mattia Donzelli, Munich (DE); Cornelis Kamerling, Munich (DE)

(73) Assignee: BRAINLAB SE, Munich (DE)

( * ) Notice: Subject to any disclaimer, the term of this patent is extended or adjusted under 35 U.S.C. 154(b) by 208 days.

(21) Appl. No.: 18/027,029

(22) PCT Filed: May 13, 2022

(86) PCT No.: PCT/EP2022/063077
§ 371 (c)(1),
(2) Date: Mar. 17, 2023

(87) PCT Pub. No.: WO2023/217391
PCT Pub. Date: Nov. 16, 2023

(65) Prior Publication Data
US 2024/0312597 A1 Sep. 19, 2024

(51) Int. Cl.
*G16H 20/40* (2018.01)
*A61N 5/10* (2006.01)
(52) U.S. Cl.
CPC ........... *G16H 20/40* (2018.01); *A61N 5/1031* (2013.01)
(58) Field of Classification Search
CPC ....... G16H 20/40; A61N 5/1031; A61N 5/103
See application file for complete search history.

(56) References Cited

U.S. PATENT DOCUMENTS

2019/0388708 A1* 12/2019 Kumar ................ A61N 5/1031

FOREIGN PATENT DOCUMENTS

EP 3530319 8/2019
EP 2598127 2/2022

OTHER PUBLICATIONS

Schlaefer, Alexander, and Achim Schweikard. "Stepwise multi-criteria optimization for robotic radiosurgery." Medical physics 35.5 (2008): 2094-2103. (Year: 2008).*
International Search Report and Written Opinion issued for Application No. PCT/EP2022/063077, 13 pages, dated May 13, 2022.
(Continued)

*Primary Examiner* — Edwin C Gunberg
*Assistant Examiner* — Richard O Toohey
(74) *Attorney, Agent, or Firm* — Gray Ice Higdon

(57) ABSTRACT

The present invention provides a computer-implemented method for determining a treatment plan for a radiotherapy treatment including a dose distribution, the method comprising the steps of determining a transition region target thickness of a transition region comprised in a low dose target volume and adjacent to a high dose target volume. The method further comprises creating shells and determining, for each of the shells, a shell-specific upper dose constraint. The method further comprises generating, by means of an optimization algorithm, a treatment plan, the optimization algorithm constrained by a predetermined lower dose constraint in the high dose target volume, an upper dose constraint in the low dose target volume, and the respective shell-specific upper dose constraint.

11 Claims, 4 Drawing Sheets

(56)  References Cited

OTHER PUBLICATIONS

Schlaefer et al., "Stepwise multi-criteria optimization for robotic radiosurgery" Medical Physics. vol. 35, No. 5, 10 pages, dated May 2008.

Reese et al., "Integral dose conservation in radiotherapy" Medical Physics, vol. 36, No. 3, 7 pages, dated Mar. 2009.

European Patent Office; Intention to Grant issued on Application No. 22727940.3, 42 pages, dated Dec. 14, 2023.

* cited by examiner

METHOD FOR DETERMINING A TREATMENT PLAN INCLUDING A DOSE DISTRIBUTION

FIELD OF THE INVENTION

The present invention relates to a computer-implemented method for determining a treatment plan including a dose distribution, a processing system, a computer program product, and a computer-readable medium.

TECHNICAL BACKGROUND

Irradiation with ionizing radiation, for example in the course of radiotherapy treatment, generally presupposes that planning is performed in advance as to how the irradiation is performed. This may be referred to as radiotherapy planning.

The planning may result in a treatment plan, which may, among others, comprise a spatial dose distribution.

Generally, the overall volume being irradiated, also referred to as target volume may be divided into sub-volumes, for example a high dose target volume, also referred to as a boost target volume or boost volume, and a low dose target volume. In case of radiotherapy irradiation, the high dose target volume may be the volume of visible disease, e.g., a tumor, and the low dose target volume may be a volume adjacent to and surrounding, at least partially, the high dose target volume.

Treatment plans, thus, may involve multilevel prescription scenario (e.g., for Cranial or Spine SRS), for example a two-level prescription scenario prescribing a higher, potentially homogeneous, dose distribution in the high dose target volume and lower dose distribution in the low dose target volume, preferably without hotspots, e.g., to decrease the risk of fracture.

Generally, a sharp dose gradient is advantageous between high dose target volume region and low dose target volume.

This is a challenging scenario for methods as currently used for treatment plan optimization, e.g., for e.g., VMAT/IMRT applications. An ideal shape of the dose distribution is not known, such that it cannot be modelled as optimization objective. Moreover, the gradient, also referred to as dose build-up from the low dose target region and the high dose target region is likely to violate dose constraints during the optimization when aiming at a sharp dose gradient. Thus, the optimization may yield numerically unstable results.

It may be possible in some scenarios for a person to manually and in a trial-and-error based manner correct the dose distribution, e.g., by changing optimization constraints or the dose gradient as such. However, this is not desirable, as it requires a skilled professional and access to data that may not be available at any given time, is cumbersome and error-prone. As a whole, this makes the currently used methods unreliable.

The present invention has the object of providing a method, processing system, computer program product, and computer-readable medium that allow for overcoming at least some of the above-identified challenges.

The present invention can be used for providing information that may be applicable to procedures e.g. in connection with a system for image-guided radiotherapy.

Aspects of the present invention, examples and exemplary steps and their embodiments are disclosed in the following.

Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The invention provides a method, a processing system, a computer program product, and a computer-readable medium according to the independent claims. Preferred embodiments are laid down in the dependent claims.

The present invention provides, among others, a computer-implemented method for determining a treatment plan for a radiotherapy treatment including a dose distribution, the method comprising the steps of determining, based on a predetermined lower dose constraint $C_{HL}$ of a high dose target volume and an upper dose constraint $C_{LU}$ of a low dose target volume surrounding and adjacent to the high dose target volume, a transition region target thickness $l_t$ of a transition region comprised in the low dose target volume and adjacent to the high dose target volume.

The method further comprises determining, based on the thickness $l_t$ a number n of shells to be created so as to form the transition region and creating n shells $S_i$, where i=0 to n−1.

The method further comprises determining, for each of the shells, a shell-specific upper dose constraint $C_{SU}(i)$ based at least on the lower dose constraint $C_{HL}$ of the high dose target volume and the upper dose constraint $C_{LU}$ of the low dose target volume, wherein the upper dose constraint of at least one of the shells is higher than the upper dose constraint $C_{LU}$ of the low dose target volume and wherein the shell-specific upper dose constraint $C_{SU}(i)$ increases from the outermost shell $S_{n-1}$ to the innermost shell $S_0$.

The method further comprises generating, by means of an optimization algorithm, a treatment plan, the optimization algorithm constrained by the predetermined lower dose constraint $C_{HL}$ in the high dose target volume, the upper dose constraint $C_{LU}$ in the low dose target volume except for the transition region, and the respective shell-specific upper dose constraint $C_{SU}(i)$ for each of the shells in the transition region.

GENERAL DESCRIPTION OF THE INVENTION

In this section, a description of the general features of the present invention is given for example by referring to possible embodiments of the invention.

The present invention provides, among others, a computer-implemented method for determining a treatment plan for a radiotherapy treatment including a dose distribution, the method comprising the steps of determining, based on a predetermined lower dose constraint $C_{HL}$ of a high dose target volume and an upper dose constraint $C_{LU}$ of a low dose target volume surrounding and adjacent to the high dose target volume, a transition region target thickness $l_t$ of a transition region comprised in the low dose target volume and adjacent to the high dose target volume.

The method further comprises determining, based on the thickness $l_t$ a number n of shells to be created so as to form the transition region and creating n shells $S_i$, where i=0 to n−1.

The method further comprises determining, for each of the shells, a shell-specific upper dose constraint $C_{SU}(i)$ based at least on the lower dose constraint $C_{HL}$ of the high dose target volume and the upper dose constraint $C_{LU}$ of the low dose target volume, wherein the upper dose constraint of at least one of the shells is higher than the upper dose constraint $C_{LU}$ of the low dose target volume and wherein the shell-specific upper dose constraint $C_{SU}(i)$ increases from the outermost shell $S_{n-1}$ to the innermost shell $S_0$.

The method further comprises generating, by means of an optimization algorithm, a treatment plan, the optimization algorithm constrained by the predetermined lower dose constraint $C_{HL}$ in the high dose target volume, the upper dose constraint $C_{LU}$ in the low dose target volume except for the transition region, and the respective shell-specific upper dose constraint $C_{SU}(i)$ for each of the shells in the transition region.

In other words, according to the present disclosure, a transition region, also referred to as a build-up region or expansion volume, with modified dose constraints may be automatically created at an interface between the high dose target volume, which may also be referred to as a boost target volume, and the low dose target volume. The transition region may be constituted by shells, which may be seen as helper volumes or helper objects. To some controlled extent, the transition region expands the high dose target volume into the low dose target volume.

The method of the present disclosure, thus, allows for reducing the effect that an optimization algorithm that is based on the dose constraint in each of the volumes yields unstable results due to inevitable constraint violation.

The method of the present disclosure, specifically, facilitates the optimization algorithm in effectively shaping the dose distribution at the interface between the low dose and high dose target volume, particularly such that the constraints are kept.

Accordingly, it is possible to generate a dose distribution for a multilevel prescription scheme with regions of differing dose constraints within a target volume.

The dose distribution as to obtain when using the method of the present disclosure thus may have a steep dose gradient between the low dose and high dose target volume, a homogeneous dose distribution in the high and low dose target volume, a high fraction of the high dose target volume that respects the lower dose constraint, and/or in general a high rate of fulfilment of the dose constraints where this is physically achievable.

The method yields dose constraints that may then be used as input for an optimization algorithm configured to output a dose distribution. Any known optimization algorithms known in the field may be used.

That is, the method of the present disclosure may comprise inputting, as input dose constraints, the predetermined higher dose constraint of the low dose target volume, the upper dose constraint of the high dose target volume and the shell-specific constraint of each of the shells into an optimization algorithm configured to output a dose distribution. The method may optionally further comprise, the optimization algorithm performing an optimization outputting a dose distribution optimized based on the input dose constraints.

The input dose constraints may further comprise a lower dose constraint of the low dose target volume and an upper dose constraint of the high dose target volume. Thus, a corridor of acceptable doses may be provided to the optimization algorithm.

The shells of the present disclosure may, for example, be nested shells

The innermost shell may be the shell adjacent to the high dose target volume. The outermost shell may be the shell that is the furthest from the high dose target volume. The number of shells may be an integer. The number of shells may be at least two, in particular at least three.

The method of the present disclosure may comprise setting initial upper dose constraints of the shells to the upper dose constraint of the low dose target region and then increasing for each of the shells, the upper dose constraint to the shell-specific dose constraint in such a manner that there is a stepwise increase of the upper dose constraint towards the high dose target volume.

The term dose distribution refers to a spatial dose distribution.

The dose distribution may represent a shape of a dose gradient, for example.

A treatment plan for a radiotherapy treatment may entail, among others, a dose distribution. The dose distribution may specify the dose dependent on spatial parameters. The treatment plan may be stored, e.g., for use as a reference for setting operating parameters for operation of a radiation beam source.

The low dose target volume surrounding and adjacent to the high dose target volume may in some cases not entail that the low dose target volume extends all the way around the high dose target volume, i.e., completely encloses the high dose target volume. For example, the high dose target volume may form at least part of the boundary of the overall target volume constituted by the low dose target volume and the high dose target volume.

A constraint, e.g., the upper and/or lower dose constraint of the low dose target volume and/or the upper and/or lower dose constraint of the high dose target volume, being predetermined, according to the present disclosure, may entail that the constraint is saved as a prescription data set, e.g., a multilevel prescription data set. Each of the constraints, may, for example, have been created by a user input via a user interface of a data processing system (also referred to as a computing system) and/or retrieved from one or more other prescription data sets.

In the present disclosure, where a first value, e.g., a dose constraint, is determined based on a second value, e.g., a predetermined dose constraint, this may entail that the second value is used as an input for a determination, e.g., calculation, of the first value.

All of the steps of the present disclosure, particularly all of the claims, may be carried out automatically, e.g., by a data processing system.

According to the present disclosure, determining, for each of the shells, the shell-specific upper dose constraint $C_{SU}(i)$ may comprise determining that $C_{SU}(0) > C_{HL}$, in particular, $C_{SU}(0) > C_{HL}$ and $C_{SU}(0) \leq C_{HU}$, in particular $C_{SU}(0) = C_{HU}$. $C_{HU}$ is an upper dose constraint of the high dose target volume, in particular, the upper dose constraint of the high dose target volume being predetermined or derived from another parameter.

$C_{SU}(0)$ is the innermost shell. Thus, in other words, the upper dose constraint of the innermost shell may be greater than the lower dose constraint of the high dose target volume. This allows for a transition into the high dose target volume that avoids violating the lower dose constraint of the high dose target volume. Optionally, in addition, the upper dose constraint of the innermost shell may be equal to or less than the upper dose constraint of the high dose target volume. This may increase the likelihood that the upper dose constraint of the high dose target volume is not violated. If the upper dose volume of the innermost shell equals the upper dose constraint of the high dose target volume, this may reduce the risk of the lower dose constraint of the high dose target volume being violated.

Alternatively or in addition, determining, for each of the shells, the shell-specific upper dose constraint $C_{SU}(i)$ may comprise determining that $$C_{SU}(i)=C_{HL}-(i-1)((C_{HL}-C_{LU})/(n-1)) \text{ for } i>0.$$

Thus, a stepwise increase of the shell-specific upper dose constraint towards the high dose target region is provided, which reduces the risk of violating the lower dose constraint in the high dose target region. Moreover, the determination as explained above is advantageous, as it yields good results with reasonable computing efforts.

The upper dose constraint for the high dose target region may in this case be greater than the lower dose constraint for the high dose target region ($C_{HU}>C_{HL}$). Moreover, the upper dose constraint of the low dose target region may be greater than the lower dose constraint of the low dose target region ($C_{LU}>C_{LL}$). In other words, dose corridors between the respective lower and upper dose constraints may be provided. Moreover, the upper dose constraint for the high dose target region is bigger than the upper dose constraint of the low dose target region ($C_{HU}>C_{LU}$).

According to the present disclosure, determining the transition region target thickness $l_t$ may be performed based on a ratio $C_{HL}/C_{LU}$ of the lower dose constraint $C_{HL}$ of the high dose target volume and the upper dose constraint $C_{LU}$ of the low dose target volume. Optionally it may be determined, additionally, on one or more parameters $a_j$, in particular, one or more parameters $a_j$ having been determined as yielding optimal dose distribution results for a given pair of values of a lower dose constraint $C_{HL}$ of the high dose target volume and a value of an upper dose constraint $C_{LU}$ of the low dose target volume.

The one or more parameters $a_j$ may have a length dimension. The transition region target thickness and/or the one or more parameters $a_j$ may depend on the specific application, e.g., the beam source or and/or a dose grid resolution. The parameters may be empirically or semi-empirically obtained parameters or theoretically determined. e.g., modelled, parameters. The method may comprise receiving or retrieving the parameters, e.g., retrieving them from a data storage and/or receiving them via a data connection, e.g., a communication channel.

Determining the transition region target thickness as explained above is advantageous, as it yields good results with reasonable computing efforts.

According to the present disclosure, determining the transition region target thickness $l_t$ may, in particular, comprise that the transition region target thickness $l_t$ is determined to be 0 if the ratio $C_{HL}/C_{LU}$ is smaller than 1 and that the transition region target thickness $l_t$ is determined to be $l_t=a_0+a_1(C_{HL}/C_{LU}-1)$, where $a_0>0$ and $a_1>0$.

As such, when lower dose constraint of the high dose target region is smaller than the upper dose constraint of the low dose target region, no transition region need be provided, as all constraints can be kept easily (e.g., even by a spatially constant dose distribution). In other cases, the transition region target thickness is determined based on different constant values, i.e., the constraints and the parameters, as specified above. This is advantageous, as it yields good results with reasonable computing efforts.

According to the present disclosure, determining the number of shells n comprises dividing the transition region target thickness $l_t$ by a predetermined shell thickness $l_s$ and truncating the remainder.

The predetermined shell thickness may depend on the specific application. e.g., the beam source characteristics and/or dose grid resolution. It may be predetermined so as to keep number of shells reasonably low for a range of estimated expected transition region target thicknesses. The predetermined shell thickness may be obtained empirically or semiempirically or theoretically determined.

Truncating the remainder means that $n=floor(l_t/l_s)$. This allows for obtaining an integer value for the number of shells irrespective of the input values for the transition region target thickness $l_t$ and the predetermined shell thickness $l_s$.

As an example, the predetermined shell thickness $l_s$ may be determined so as to be larger than or equal to the dose grid resolution.

An exemplary range for suitable values for the predetermined shell thickness is $l_s$ being equal to or greater than 0.5 mm, particularly 0.75 mm, and equal to or lower than 2 mm, particularly 1.5 mm. In particular, $l_s$ may be 1 mm.

The values of the one or more parameters and the predetermined shell thickness may be constrained such that the number of shells is equal to or greater than 2, in particular greater than 2.

According to the present disclosure, determining the number of shells n may comprise determining that n equals a number of shells $n_{ini}$ obtained by the steps of dividing the transition region target thickness $l_t$ by the predetermined shell thickness $l_s$ and truncating the remainder.

Determining the number of shells n may comprise determining whether a/the number of shells $n_{ini}$ obtained by the steps of dividing the transition region target thickness $l_t$ by the predetermined shell thickness $l_s$ and truncating the remainder exceeds a predetermined threshold $n_{max}$ and, if this is the case, determining that the number of shells n equals $n_{max}$ and otherwise determining that the number of shells n equals $n_{ini}$.

That is, the method may comprise determining the number of shells in such a manner it does not exceed a predetermined threshold, which may, for example, be set so as to limit computing resources required for an optimization performed to obtain the dose distribution. An exceedingly high number of shells may increase the required computing resources in a manner that is not justified by the improvement of the resulting dose distribution.

According to the present disclosure, the above-mentioned one or more parameters $a_j$, in particular, $a_0$ and $a_1$, may be parameters determined by solving a plurality of optimization problems for each of different sets of dose constraints and different sets of parameters $a_j$, and by selecting, the one or more parameters $a_j$ yielding optimal dose distribution results for a given pair of values of a lower dose constraint $C_{HL}$ of the high dose target volume and a value of an upper dose constraint $C_{LU}$ of the low dose target volume, the selecting based on one or more criteria including at least one of homogeneity of the resulting dose distribution in the high dose target volume, constraint violation, steepness of the dose gradient from low dose target volume to high dose target volume, and stability of the resulting solution of the optimization problem.

In particular, the selecting may be performed making use of a grid search.

In terms of homogeneity, parameters representative of homogeneity may comprise, among others, the presence, absence, and/or number of hotspots. In terms of dose variations, criteria may comprise which constraints are violated, how many constraints are violated and/or by what amount constraints are violated.

Using parameters obtained as described above allow for the method of the present disclosure yielding accurate and stable results for a wide range of scenarios and applications without requiring a computationally expensive and complex determination of the shells and dose constraints of the shells.

The method of the present disclosure may comprise determining the one or more parameters $a_j$, e.g., as outlined above. The parameters, in particular, may be determined prior to determining the transition region thickness and/or prior to determining the predetermined dose constraints mentioned above.

Alternatively or in addition, the method of the present disclosure may comprise, prior to the creating of the n shells, performing a 3D segmentation of the high dose target volume and the low dose target volume. The segmentation of the low dose target volume and/or high dose target volume may be performed using any segmentation methods known in the art, e.g., Atlas segmentation. The segmentation yields a 3D mathematical representation of the respective target volume. This may be advantageous for a reliable determination of the boundaries of the high dose and/or low dose target volume.

According to the present disclosure, the upper dose constraint $C_{LU}$ may be a predetermined upper dose constraint, particularly received via a user input and/or retrieved from a data storage, e.g., a data base. Alternatively, the upper dose constraint may be derived from another parameter, particularly from $C_{HL}$. The deriving may optionally be performed by means of an algorithm. $C_{LU}$ may, for example, be determined as having the same value as $C_{HL}$.

All of the steps of the method of the present disclosure may be performed by a data processing system, in particular, fully automatically. In particular, predetermined values, e.g., the predetermined constraints and/or the parameters $a_j$ may be accessed automatically, even though they may have been entered manually at some point.

The invention also provides a data processing system configured to carry out the method of the present disclosure, that is one or more, in particular all of the steps of the method of the present disclosure. In particular, the data processing system may comprise one or more processors configured to perform one or more, in particular all of the steps of the method of the present disclosure.

The invention also provides computer program product comprising instructions which, when the program is executed by a computer, cause the computer to carry out the method of the present disclosure, that is one or more, in particular all of the steps of the method of the present disclosure.

The invention also provides a computer-readable medium comprising instructions which, when executed by a computer, cause the computer to carry out the method of the present disclosure, that is one or more, in particular all of the steps of the method of the present disclosure.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to providing output that may be used for determining settings for operating machine providing a beam, the output and/or settings allowing for meeting given spatial dose constraints. For this reason alone, no surgical or therapeutic activity and in particular no surgical or therapeutic step is necessitated or implied by carrying out the invention.

The features and advantages outlined above in the context of the method similarly apply to the processing system, the medial system, the computer program product, and the computer readable medium, of the present disclosure.

Definitions

In this section, definitions for specific terminology used in this disclosure are offered which also form part of the present disclosure Computer Implemented Method The method in accordance with the invention is a computer implemented method. For example, all the steps or merely some of the steps (i.e. less than the total number of steps) of the method in accordance with the present disclosure can be executed by a processing system, e.g. a computer (for example, at least one computer) of the processing system. An embodiment of the computer implemented method is a use of the processing system, e.g., the computer, for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The present disclosure also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the present disclosure, computer program elements can be embodied by hardware and/or software (this includes firmware, resident software, microcode, etc.). Within the framework of the present disclosure, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer: a computer can be a data processing device comprising means for executing the computer program elements and/or the program in accordance with the present disclosure, for example a data processing device comprising a digital processor (central processing unit or CPU) which executes the computer program elements, and optionally a volatile memory (for example a random access memory or RAM) for storing data used for and/or produced by executing the computer program elements. Within the framework of the present disclosure, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the present disclosure in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Atlas/Atlas Segmentation

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

Treatment Beam

The present disclosure relates to the field of controlling a treatment beam. The treatment beam treats body parts which are to be treated and which are referred to in the following as "treatment body parts". These body parts are for example parts of a patient's body, i.e. anatomical body parts.

The present disclosure relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/health-care_us_elekta_vmat.php and http://www.varian.com/us/oncology/treatments/treatment_techniques/rapidarc.

BRIEF DESCRIPTION OF THE DRAWINGS

In the following, the invention is described with reference to the appended figures which give background explanations and represent specific embodiments of the invention.

The scope of the invention is however not limited to the specific features disclosed in the context of the figures, wherein.

DESCRIPTION OF EMBODIMENTS

Figure 1:
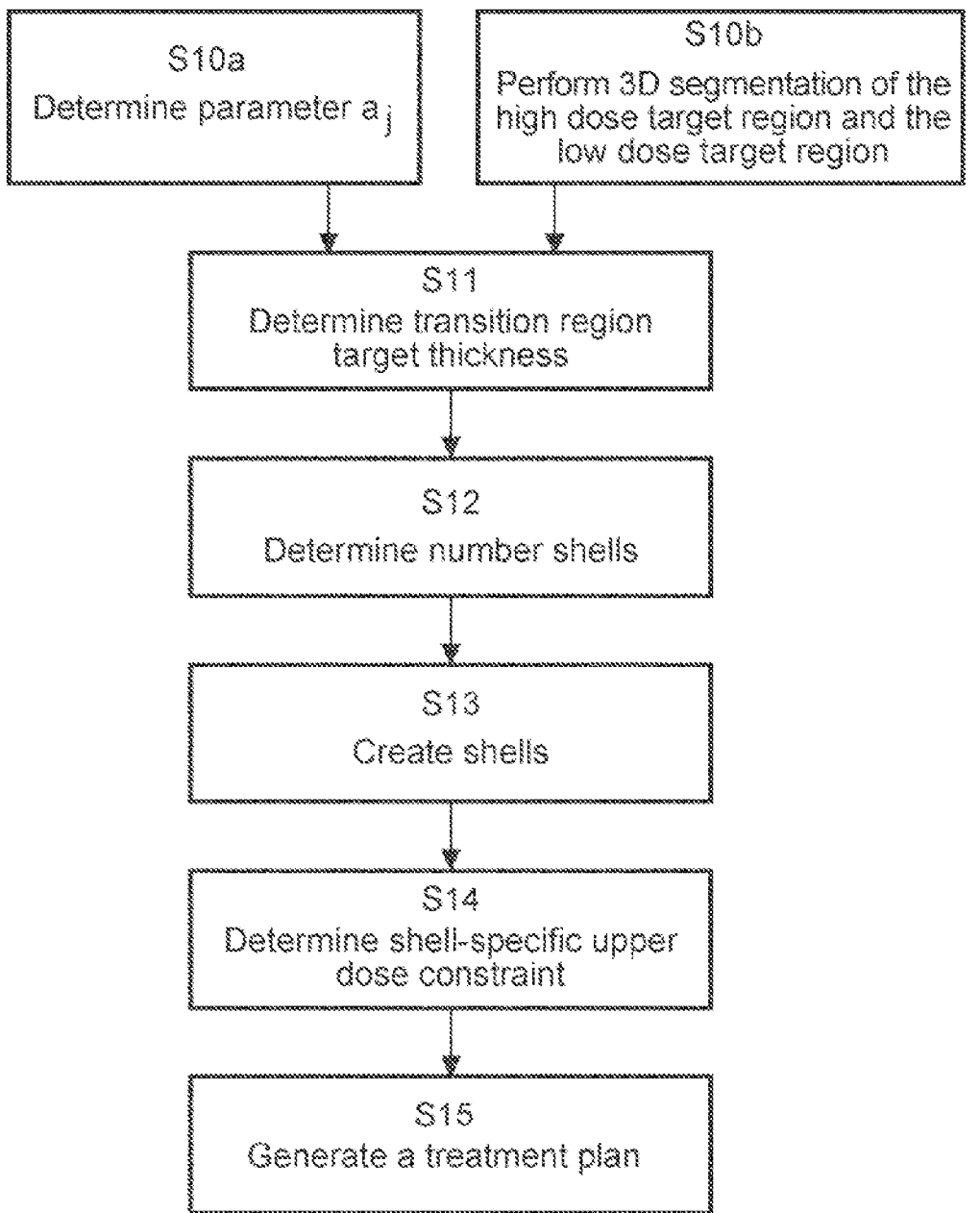
FIG. 1 illustrates a method according to the present disclosure.

FIG. 1 illustrates exemplary steps of a computer-implemented method for determining a treatment plan for a radiotherapy treatment including a dose distribution according to the present disclosure.

The method comprises the step S11 of determining, based on a predetermined lower dose constraint $C_{HL}$ of a high dose target volume and a, in this example predetermined, upper dose constraint $C_{LU}$ of a low dose target volume surrounding and adjacent to the high dose target volume, a transition region target thickness $l_t$ of a transition region comprised in the low dose target volume and adjacent to the high dose target volume. The shell thickness $l_s$ may, for example, be determined so as to be larger than or equal to the dose grid resolution. The present example refers to an upper dose constraint $C_{LU}$ of the low dose target volume being a predetermined constraint, which may, for example, be input by a user and/or retrieved from a stored data set. However, alternatively, the upper dose constraint $C_{LU}$ of the low dose target volume may also be calculated, e.g., derived from values set for other parameters. An algorithm may be employed for this purpose.

For example, determining the transition region target thickness $l_t$ may be performed based on a ratio $C_{HL}/C_{LU}$ of the lower dose constraint $C_{HL}$ of the high dose target volume and the upper dose constraint $C_{LU}$ of the low dose target volume and optionally one or more parameters $a_j$, in particular, one or more parameters $a_j$ having been determined as yielding optimal dose distribution results for a given pair of values of a lower dose constraint $C_{HL}$ of the high dose target volume and a value of an upper dose constraint $C_{LU}$ of the low dose target volume.

The transition region target thickness $l_t$ may, for example, be determined to be 0 if the ratio $C_{HL}/C_{LU}$ is smaller than 1, as in that case no transition region is required for yielding reliable results, and the transition region target thickness $l_t$ may otherwise be determined to be $l_t=a_0+a_1(C_{HL}/C_{LU}-1)$, where $a_0>0$ and $a_1>0$.

The method further comprises the step S12 of determining, based on the thickness $l_t$, a number n of shells to be created so as to form the transition region. For example, the number of shells n may result from dividing the transition region target thickness $l_t$ by a predetermined shell thickness $l_s$ and truncating the remainder.

The number of shells may, however, optionally be limited, e.g., by determining whether a number of shells $n_{tmi}$ obtained by the steps of dividing the transition region target thickness $l_t$ by the predetermined shell thickness $l_s$ and truncating the remainder exceeds a predetermined threshold $n_{max}$ and, if this is the case, determining that the number of shells n equals $n_{max}$ and otherwise determining that the number of shells n equals $n_{ini}$.

The method further comprises the step S13 of creating n shells SL where i=0 to n−1. The innermost shell is $S_0$.

The method further comprises the step S14 of determining, for each of the shells, a shell-specific upper dose constraint $C_{SU}(i)$ based at least on the lower dose constraint $C_{HL}$ of the high dose target volume and the upper dose constraint $C_{LU}$ of the low dose target volume. The upper dose constraint of at least one of the shells is higher than the upper dose constraint $C_{LU}$ of the low dose target volume and the shell-specific upper dose constraint $C_{SU}(i)$ increases from the outermost shell $S_{n-1}$ to the innermost shell $S_0$.

As an example, for each of the shells, the shell-specific upper dose constraint $C_{SU}(i)$ may be determined as follows:

$C_{SU}(0)>C_{HL}$, in particular, $C_{SU}(0)>C_{HL}$ and $C_{SU}(0){\leq}C_{HU}$, in particular $C_{SU}(0)=C_{HU}$,
wherein $C_{HU}$ is a, for example predetermined, upper dose constraint of the high dose target volume, and $$C_{SU}(i)=C_{HL}-(i-1)((C_{HL}-C_{LU})/(n-1)) \text{ for } i>0.$$

The method further comprises the step S15 of generating, by means of an optimization algorithm, a treatment plan, the optimization algorithm constrained by the predetermined lower dose constraint $C_{HL}$ in the high dose target volume, the upper dose constraint $C_{LU}$ in the low dose target volume except for the transition region, and the respective shell-specific upper dose constraint $C_{SU}(i)$ for each of the shells in the transition region.

The method may also comprise the optional step S10a of determining the one or more parameters $a_j$ used for determining the transition region target thickness $l_t$ in step S11. For example, the one or more parameters $a_j$, in particular, $a_0$ and $a_1$, may be determined by solving a plurality of optimization problems for each of different sets of dose constraints and different sets of parameters $a_j$, and by selecting, the one or more parameters $a_j$ yielding optimal dose distribution results for a given pair of values of a lower dose constraint $C_{HL}$ of the high dose target volume and a value of an upper dose constraint $C_{LU}$ of the low dose target volume, the selecting based on one or more criteria including at least one of homogeneity of the resulting dose distribution in the high dose target volume, constraint violation, steepness of the dose gradient from low dose target volume to high dose target volume, and stability of the resulting solution of the optimization problem.

For example, $a_0>2$ mm for $l_s=1$ mm, in particular, $a_0=2.2$ and $a_1=8.9$ mm. Moreover, $a_0$ may be set such that the number of shells n may be equal to or greater than 2 for $C_{HL}=C_{LU}$.

The method may alternatively or in addition comprise, prior to the creating of the n shells, the optional step S10b of performing a 3D segmentation of the high dose target volume and the low dose target volume.

A detailed example of a method according to the present disclosure is provided below.

3D segmentation data of the high dose target volume or region (called boost target volume), 3D segmentation of the low dose target volume or region, the lower and upper dose constraint on the boost target volume, and the upper dose constraint on the low dose target volume, may serve as input data.

A set of shell-shaped helper objects, also referred to as shell objects or shells, may be generated by expanding the boost target volume with a fixed margin, i.e., creating in the low dose target region a transition region having a transition region target thickness $l_t$ that equals the margin.

The margin equals the total thickness of the summarized thicknesses of all shell objects. It is determined by the ratio $$C_{HL}/C_{LU}$$

where $C_{HL}$ is the boost target volume lower dose constraint and $C_{LU}$ is the low dose target volume upper dose constraint.

$$l = a_0 + a_1 * (C_{HL}/C_{LU} - 1),$$

where $a_0$ and $a_1$ are constants of the dimension length.

In case $C_{HL}<C_{LU}$, $l_t$ is set to zero and no shells are generated.

The number n of shell objects is determined by dividing $l_t$ by 1 mm and truncating the remainder.

$$n = \text{floor}(l_t / 1 \text{ mm})$$

The thickness $l_s$ of each shell is $l_t/n$.

The constant $a_0$ is greater than 2 mm and $a_1$ is positive, therefore it is ensured that at least two shells are generated in any case where $l_t>0$.

The shell objects are intersected with the low dose target volume and only the intersection volume is kept. In other words, any volume falling completely outside of the overall target volume is not included in determining the dose distribution, e.g., in an optimization.

The shells are indexed from i=0 to n−1 from the innermost to the outermost shell.

Within these shells the target volume upper constraint is replaced with modified values.

In the innermost shell (i=0), the upper dose constraint is set to the boost target volume upper dose constraint.

$$C_{SU}(0)=C_{HU}$$

In the remaining shells i=1 to n−1 the upper dose constraint is determined as follows:

$$C_{SU}(i) = C_{HL}-(i-1)*((C_{HL} - C_{LU})/(n-1))$$

As a result, a transition region around the boost target volume is defined where the upper dose constraint is increased stepwise towards the boost target volume. This allows the optimization algorithm to generate a steep dose gradient between target volume and boost target volume without violating the dose constraints.

The constants $a_0$ and $a_1$ may be determined by a grid search where a large set of treatment optimization problems with different prescriptions was solved with our stochastic optimization algorithm trying out different values for $a_0$ and $a_1$.

The homogeneity of the dose in the boost target volume was taken as measure for the best planning result and $a_0$ and $a_1$ were then selected accordingly.

Reasonable choices for these constants would be $a_0=2.5$ mm and $a_1=8.5$ mm.

Hereinbelow are listed exemplary values for shell parameters and constraints for two different sets of input target volume constraints.

Example 1

Target Volume Constraints:

$$C_{LU} = 15 \text{ } Gy, C_{HL} = 30 \text{ } Gy, C_{HU} = 33 \text{ } Gy$$

RESULTING parameters.

$$l_t = 11 \text{ mm}, n = 11,$$

$$C_{SU}(0) = 33 \text{ } Gy,$$

$$C_{SU}(1) = 30 \text{ } Gy,$$

$$C_{SU}(2) = 28.5 \text{ } Gy,$$

$$C_{SU}(3) = 27 \text{ } Gy, \dots ,$$

$$C_{SU}(10) = 16.5 \text{ } Gy$$

Example 2

Target Volume Constraints:

$$C_{LU} = 20 \text{ } Gy,$$

$$C_{HL} = 24 \text{ } Gy,$$

$$C_{HU} = 28 \text{ } Gy$$

Resulting Parameters:

$$l_t = 4.2 \text{ mm}, n = 4,$$

$$C_{SU}(0) = 28 \text{ } Gy,$$

$$C_{SU}(1) = 24 \text{ } Gy,$$

$$C_{SU}(2) = 22.67 \text{ } Gy,$$

$$C_{SU}(3) = 21.33 \text{ } Gy$$

Figure 2A:
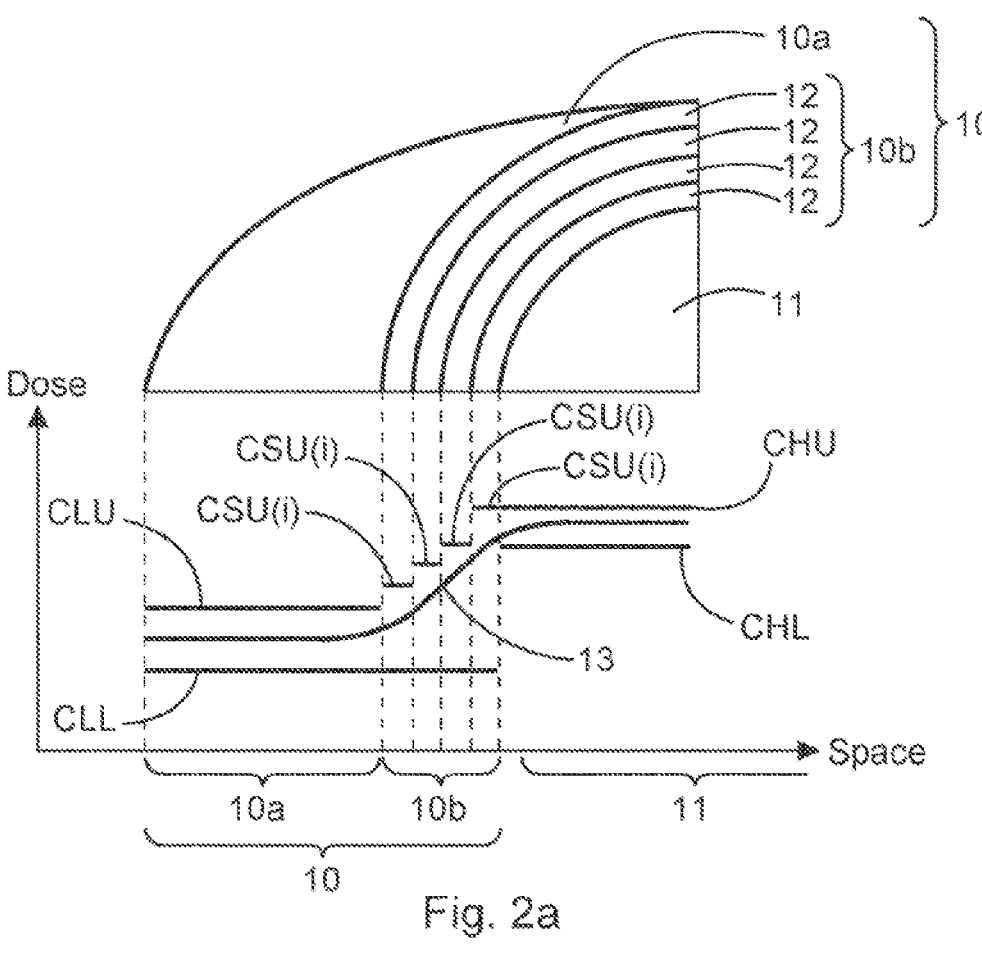
FIGS. 2a to 2d schematically illustrate different dose distributions.

In FIG. 2*a*, the low dose target volume 10, high dose target volume 11, and several shells 12 are shown. A transition target region 10*b* is formed by the shells. The remaining volume of the low dose target volume (outside of the target region) is labelled 10*a*.

Moreover, the predetermined lower dose constraint $C_{HL}$ of the high dose target volume and an, for example predetermined, upper dose constraint $C_{LU}$ of the low dose target volume are shown. In addition, an, for example predetermined, upper dose constraint $C_{HU}$ of the high dose target volume and a predetermined lower dose constraint $C_{LL}$ of the low dose target volume are shown. In addition, the respective shell-specific upper dose constraint $C_{SU}(i)$ for each of the shells in the transition region is shown. It can be seen that the constraint increases towards the high dose target volume and, particularly, in the present disclosure, the innermost shell has an upper dose constraint that equals the upper dose constraint of the high dose target volume.

An exemplary dose distribution 13 as obtained when applying the method of the present disclosure is also shown.

Figure 2B:
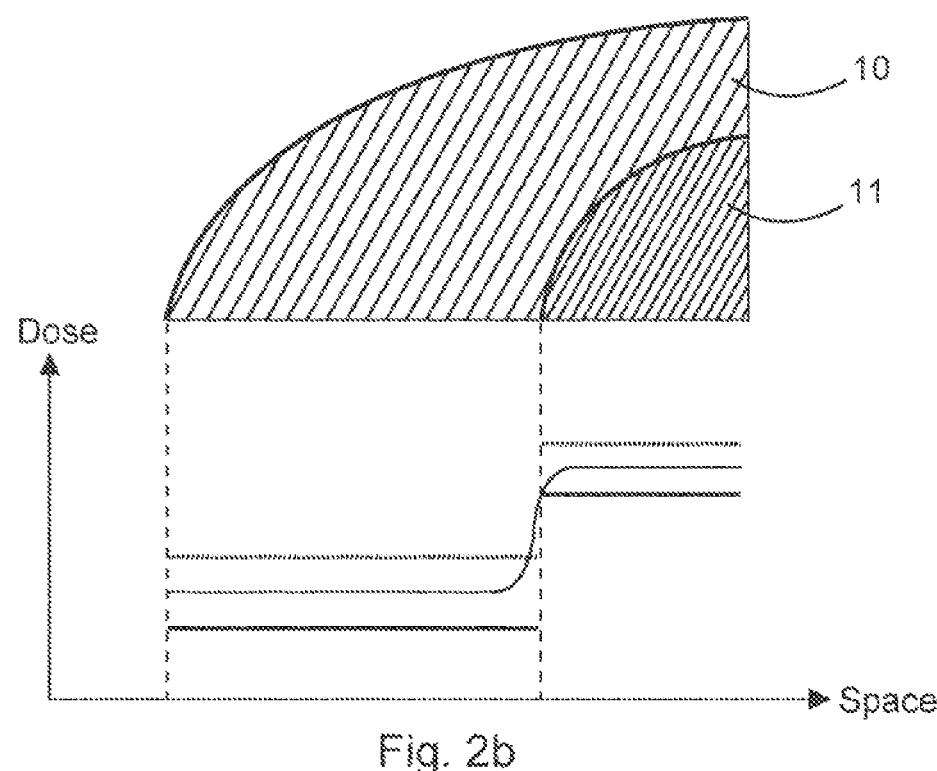

An ideal dose distribution is shown in FIG. 2*b*. It can be seen that the dose distribution is relatively steep at the interface between low dose target volume and high dose target volume, that no violations are created, and that the dose distribution is homogenous in each of the regions.

Figures 2C, 2D:
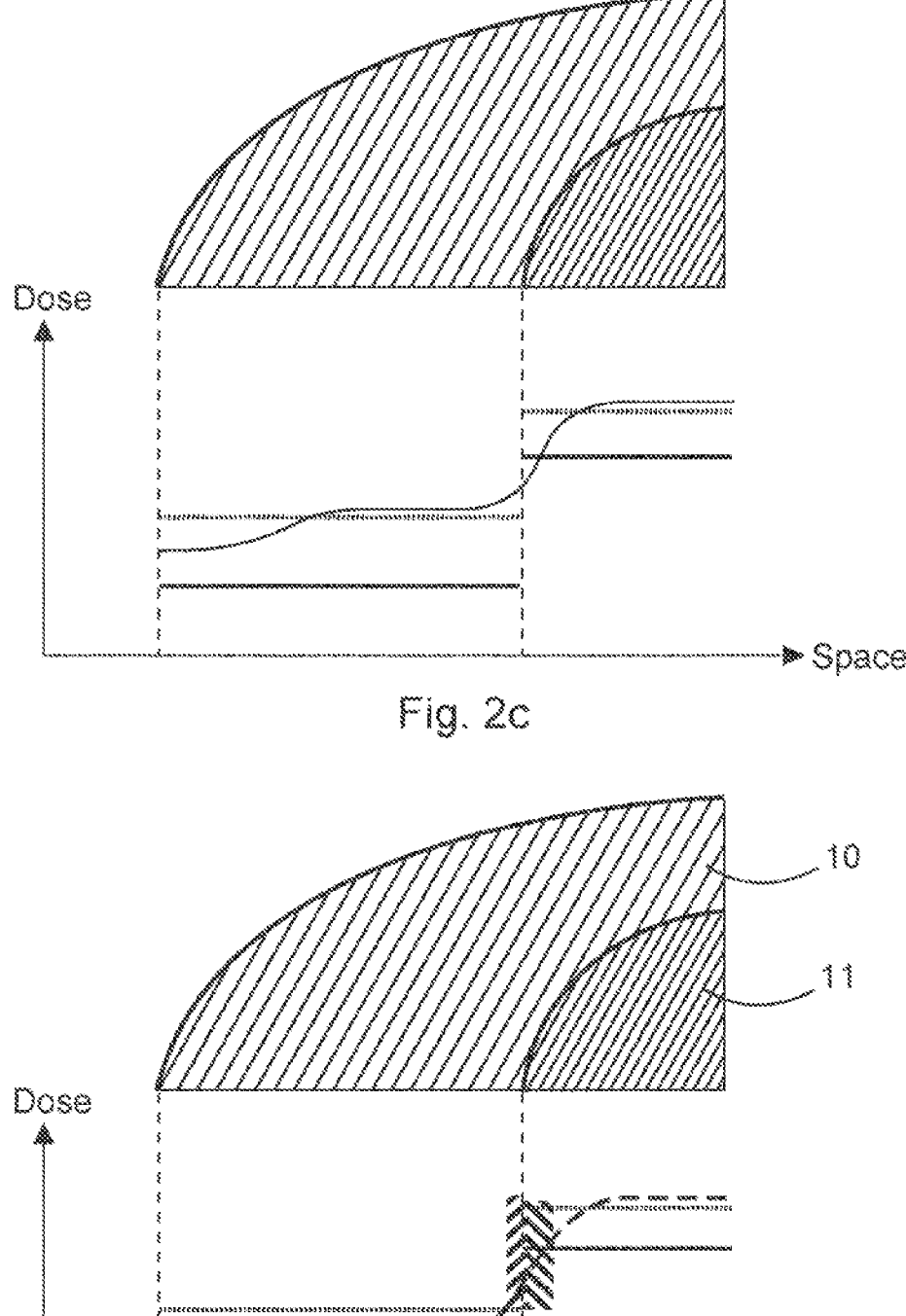

FIGS. 2*c* and 2*d* show dose distributions as obtained by prior art systems. It is immediately apparent that the dose distribution of the present disclosure. e.g., as shown in FIG. 2*a*, is closer to the ideal dose distribution of FIG. 2*b* compared to the dose distributions in FIGS. 2*c* and 2*d* of the prior art.

FIG. 2*c* shows a dose distribution wherein the upper dose constraint is exceeded over an extended region towards the interface between low dose and high dose target volume. Moreover, although the transition is steep within the low dose target volume, it flattens in the high dose target volume, leading to a lower dose violation at the interface an inhomogeneity where the dose increases gradually and an adjacent region with an upper dose violation. Accordingly, an insufficient and inhomogeneous dose is provided for a significant part of the high dose target volume and an exceedingly high dose is obtained for significant parts of the high dose and the low dose target volumes.

In FIG. 2*d*, an interface region at an interface of high dose and low dose target volume, where a dose violation may be allowed (e.g., by a low penalty in an optimization algorithm), is provided (shown as the hatched region). The transition has a steeper shape than in FIG. 2*c*. However, nonetheless, an inhomogeneity occurs in the high dose target volume, to an extent where even the upper dose constraint in the high dose target volume is exceeded in an area close to the interface between the low dose and high dose target volume. This may be, due to the constraint violations in the hatched interface region.

Figure 3:
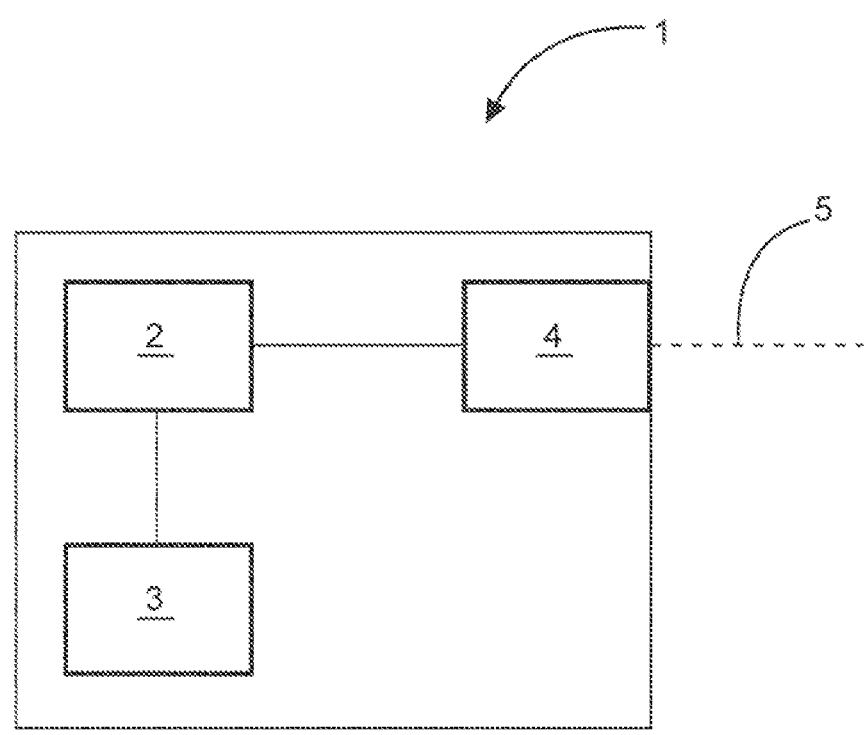
FIG. 3 is a schematic illustration of the system according to the present disclosure.

In FIG. 3, a schematic illustration of a data processing system 1 according to the present disclosure. The data processing system may comprise at least processing means 2 and storage means 3, which may comprise temporary memory, e.g., RAM, and/or permanent memory, e.g., ROM. Moreover, optionally the processing system may comprise one or more communication interfaces 4 for receiving and transmitting data via one or more data connections 5. For example, the processing system may comprise one or more computers.

While the invention has been illustrated and described in detail in the drawings and foregoing description, such illustration and description are to be considered exemplary and not restrictive. The invention is not limited to the disclosed embodiments. In view of the foregoing description and drawings it will be evident to a person skilled in the art that various modifications may be made within the scope of the invention, as defined by the claims.

The invention claimed is:

1. A computer-implemented method:
   determining, based on a predetermined lower dose constraint $C_{HL}$ of a high dose target volume and an upper dose constraint $C_{LU}$ of a low dose target volume surrounding and adjacent to the high dose target volume, a transition region target thickness $l_t$ of a transition region comprised in the low dose target volume and adjacent to the high dose target volume;
   determining, based on the thickness $l_t$ a number n of shells to be created so as to form the transition region;
   creating n shells $S_i$, where i=0 to n−1;
   determining, for each of the shells, a shell-specific upper dose constraint $C_{SU}(i)$ based at least on the lower dose constraint $C_{HL}$ of the high dose target volume and the upper dose constraint $C_{LU}$ of the low dose target volume, wherein the upper dose constraint of at least one of the shells is higher than the upper dose constraint $C_{LU}$ of the low dose target volume and wherein the shell-specific upper dose constraint $C_{SU}(i)$ increases from the outermost shell $S_{n-1}$ to the innermost shell $S_0$; and generating, by an optimization algorithm, a treatment plan, the optimization algorithm constrained by the predetermined lower dose constraint $C_{HL}$ in the high dose target volume, the upper dose constraint $C_{LU}$ in the low dose target volume except for the transition region, and the respective shell-specific upper dose constraint $C_{SU}(i)$ for each of the shells in the transition region;

wherein the method further includes:

determining the transition region target thickness $l_t$ is performed based on a ratio $C_{HL}/C_{LU}$ of the lower dose constraint $C_{HL}$ of the high dose target volume and the upper dose constraint $C_{LU}$ of the low dose target volume and optionally one or more parameters $a_j$ having been determined as yielding optimal dose distribution results for a given pair of values of a lower dose constraint $C_{HL}$ of the high dose target volume and a value of an upper dose constraint $C_{LU}$ of the low dose target volume.

2. The method of claim 1, wherein determining, for each of the shells, the shell-specific upper dose constraint $C_{SU}(i)$ comprises determining that $$C_{SU}(0) > C_{HL} \text{ and } C_{SU}(0) \le C_{HU},$$

wherein $C_{HU}$ is an upper dose constraint of the high dose target volume, in particular, the upper dose constraint of the high dose target volume being predetermined or derived from another parameter, and $$C_{SU}(i) = C_{HL} - (i-1)((C_{HL} - C_{LU})/(n-1)) \text{ for } i > 0.$$

3. The method of claim 1, wherein determining the transition region target thickness $l_t$ comprises that the transition region target thickness $l_t$ is determined to be 0 if the ratio $C_{HL}/C_{LU}$ is smaller than 1 and that the transition region target thickness $l_t$ is determined to be $l_t = a_0 + a_1(C_{HL}/C_{LU} - 1)$, where $a_0 > 0$ and $a_1 > 0$.

4. The method of claim 1, wherein the predetermined shell thickness $l_s$ is determined so as to be larger than or equal to a dose grid resolution.

5. The method of claim 1, wherein the one or more parameters $a_0$ and $a_1$, are parameters determined by solving a plurality of optimization problems for each of different sets of dose constraints and different sets of parameters $a_j$, and by selecting, the one or more parameters $a_j$ yielding optimal dose distribution results for a given pair of values of a lower dose constraint $C_{HL}$ of the high dose target volume and a value of an upper dose constraint $C_{LU}$ of the low dose target volume, the selecting based on one or more criteria including at least one of homogeneity of the resulting dose distribution in the high dose target volume, constraint violation, steepness of a dose gradient from low dose target volume to high dose target volume, and stability of the resulting solution of the optimization problem.

6. The method of claim 1, further comprising, prior to the creating of the n shells, performing a 3D segmentation of the high dose target volume and the low dose target volume.

7. The method of claim 1, wherein the upper dose constraint $C_{LU}$ is a predetermined upper dose constraint received via a user input and/or retrieved from a data storage, or wherein the upper dose constraint is derived from $C_{HL}$.

8. The method of claim 1, wherein the method further includes:

determining the number of shells n comprises dividing the transition region target thickness $l_t$ by a predetermined shell thickness $l_s$ and truncating the remainder.

9. The method of claim 8, wherein determining the number of shells n further comprises determining that n equals a number of shells $n_{ini}$ obtained by the steps of dividing the transition region target thickness $l_t$ by the predetermined shell thickness $l_s$ and truncating the remainder.

10. The method of claim 8, wherein determining the number of shells n further comprises determining whether a number of shells $n_{ini}$ obtained by the steps of dividing the transition region target thickness $l_t$ by the predetermined shell thickness $l_s$ and truncating the remainder exceeds a predetermined threshold $n_{max}$ and, if this is the case, determining that the number of shells n equals $n_{max}$ and otherwise determining that the number of shells n equals $n_{ini}$.

11. A non-transitory computer-readable medium comprising instructions which, when executed by a computer, cause the computer to determine, based on a predetermined lower dose constraint $C_{HL}$ of a high dose target volume and a upper dose constraint $C_{LU}$ of a low dose target volume surrounding and adjacent to the high dose target volume, a transition region target thickness $l_t$ of a transition region comprised in the low dose target volume and adjacent to the high dose target volume;

determine, based on the thickness $l_t$ a number n of shells to be created so as to form the transition region;

create n shells $S_i$, where i=0 to n–1;

determine, for each of the shells, a shell-specific upper dose constraint $C_{SU}(i)$ based at least on the lower dose constraint $C_{HL}$ of the high dose target volume and the upper dose constraint $C_{LU}$ of the low dose target volume, wherein the upper dose constraint of at least one of the shells is higher than the upper dose constraint $C_{LU}$ of the low dose target volume and wherein the shell-specific upper dose constraint $C_{SU}(i)$ increases from the outermost shell $S_{n-1}$ to the innermost shell $S_0$; and generate, by an optimization algorithm, a treatment plan, the optimization algorithm constrained by the predetermined lower dose constraint $C_{HL}$ in the high dose target volume, the upper dose constraint $C_{LU}$ in the low dose target volume except for the transition region, and the respective shell-specific upper dose constraint $C_{SU}(i)$ for each of the shells in the transition region;

wherein the instructions further cause the computer to:

determine the transition region target thickness $l_t$ is performed based on a ratio $C_{HL}/C_{LU}$ of the lower dose constraint $C_{HL}$ of the high dose target volume and the upper dose constraint $C_{LU}$ of the low dose target volume and optionally one or more parameters $a_j$ having been determined as yielding optimal dose distribution results for a given pair of values of a lower dose constraint $C_{HL}$ of the high dose target volume and a value of an upper dose constraint $C_{LU}$ of the low dose target volume.

* * * * *